(12) United States Patent
Eaton (10) Patent No.: US 8,932,254 B2
(45) Date of Patent: Jan. 13, 2015

(54) SYRINGE SAFETY SHIELDS AND AUTOINJECTOR

(75) Inventor: Mark Eaton, Oxfordshire (GB)

(73) Assignee: Owen Mumford Limited, Oxford (GB)

( * ) Notice: Subject to any disclaimer, the term of this patent is extended or adjusted under 35 U.S.C. 154(b) by 565 days.

(21) Appl. No.: 13/061,780

(22) PCT Filed: Aug. 28, 2009

(86) PCT No.: PCT/GB2009/051095
§ 371 (c)(1),
(2), (4) Date: Apr. 1, 2011

(87) PCT Pub. No.: WO2010/026414
PCT Pub. Date: Mar. 11, 2010

(65) Prior Publication Data
US 2011/0172602 A1    Jul. 14, 2011

Related U.S. Application Data

(60) Provisional application No. 61/099,731, filed on Sep. 24, 2008.

(30) Foreign Application Priority Data

Sep. 2, 2008  (GB) .................................. 0815923.8

(51) Int. Cl.
*A61M 5/20* (2006.01)
*A61M 5/32* (2006.01)
*A61M 5/24* (2006.01)

(52) U.S. Cl.
CPC ........... *A61M 5/2033* (2013.01); *A61M 5/3243* (2013.01); *A61M 5/24* (2013.01); *A61M 5/326* (2013.01); *A61M 2005/2414* (2013.01); *A61M 2005/3247* (2013.01)
USPC ........................................................ 604/135

(58) Field of Classification Search
USPC ........... 604/110, 135, 136, 137, 154; 606/108
See application file for complete search history.

(56) References Cited

U.S. PATENT DOCUMENTS 5,156,599 A * 10/1992 Ranford et al. ............... 604/198
5,358,489 A * 10/1994 Wyrick .......................... 604/136
(Continued)

FOREIGN PATENT DOCUMENTS

EP    0666084 A2    8/1995
EP    0864335 A2    9/1998
(Continued)

OTHER PUBLICATIONS

British Search Report, dated Dec. 22, 2008, from corresponding British application.
(Continued)

*Primary Examiner* — Manuel Mendez
(74) *Attorney, Agent, or Firm* — Young & Thompson (57) ABSTRACT

A disposable syringe assembly for use in an autoinjector device, or manually includes a syringe housing which receives the syringe barrel and which is restrained against longitudinal movement with respect thereto, a shield portion mounted for generally telescopic movement relative to the syringe housing between a retracted position and an extended position in which in use it shields the syringe needle, and a lock out arrangement activated as the shield moves towards its extended position to prevent retraction therefrom. When fitted in an autoinjector the autoinjector may include drive mechanism for moving the shield portion to its locked out extended position, whereby, on completion of an injection operation, the disposable syringe assembly may be removed from the autoinjector in a shielded condition for subsequent disposal.

19 Claims, 11 Drawing Sheets

(56) References Cited

U.S. PATENT DOCUMENTS

| | | | |
|---|---|---|---|
| 6,099,503 A | 8/2000 | Stradella | |
| 6,544,234 B1* | 4/2003 | Gabriel | 604/207 |
| 6,673,035 B1* | 1/2004 | Rice et al. | 604/72 |
| 2001/0005781 A1 | 6/2001 | Bergens et al. | |
| 2001/0049496 A1 | 12/2001 | Kirchhofer et al. | |
| 2003/0078546 A1 | 4/2003 | Jensen | |
| 2004/0225262 A1* | 11/2004 | Fathallah et al. | 604/198 |
| 2007/0112310 A1* | 5/2007 | Lavi et al. | 604/245 |
| 2011/0106008 A1* | 5/2011 | Kronestedt | 604/110 |

FOREIGN PATENT DOCUMENTS

| | | | |
|---|---|---|---|
| GB | 2283425 A | 5/1995 | |
| WO | 95/04562 A1 | 2/1995 | |
| WO | 99/06100 A2 | 2/1999 | |
| WO | 01/17593 A1 | 3/2001 | |
| WO | 2004/069302 A2 | 8/2004 | |
| WO | 2005/009520 A1 | 2/2005 | |
| WO | 2006/052737 A1 | 5/2006 | |
| WO | 2006/057604 A1 | 6/2006 | |

OTHER PUBLICATIONS

International Search Report, dated Dec. 18, 2009, from corresponding PCT application.

* cited by examiner

SYRINGE SAFETY SHIELDS AND AUTOINJECTOR

This application is a Section 371 National Stage of International Application PCT/GB2009/051095 filed on Aug. 28, 2009, which claims priority of U.K. patent application no. GB 0815923.8, filed Sep. 2, 2008; and U.S. provisional application no. 61/099,731, filed Sep. 24, 2008.

FIELD OF THE INVENTION

This invention relates to syringe safety shields and in particular, but not exclusively, to such arrangements used in a disposable syringe arrangement for use in an autoinjector.

BACKGROUND OF THE INVENTION

There is a growing demand for reusable autoinjectors and for a reduction in the amount of materials or components that have to be disposed of. At the same time, safety requirements demand that, after use, the disposable components are in a safe state to reduce the risk of needle stick injuries. There is also a need for a syringe safety shield assembly that can be used either manually where an autoinjector is not available, or in an autoinjector, in each case providing needle stick protection post injection. There are many known arrangements for shrouding the needle on a syringe after a manual injection has been effected. There are also many arrangements for disposable autoinjectors which shroud the needle after use. However, there is a need for a syringe safety shield arrangement which can be used in a number of different applications, including in an autoinjector and in which there is a low number of components.

Although autoinjectors that provide a lock out needle shield for shielding the needle on completion of an injection are known, such devices either are designed as single use disposable autoinjectors, with the consequential environmental impact, or multiple use injectors in which the spent syringe is removed, allowing reuse of the autoinjector, but without shielding of the needle.

SUMMARY OF THE INVENTION

Accordingly, in one aspect, this invention provides an autoinjector system comprising an autoinjector device having a housing for receiving a disposable syringe assembly comprising a syringe having a syringe barrel, a needle at the forward end and a plunger, in combination with a safety shield arrangement, comprising:

a syringe housing receiving said syringe barrel and restrained against longitudinal movement with respect thereto, a shield portion mounted for generally telescopic movement relative to said syringe housing between a retracted position and an extended position in which in use it shields said syringe needle, and a lock out arrangement effective as said shield moves towards its extended position to prevent retraction therefrom, the autoinjector including a drive mechanism for advancing said syringe to an injection position, for driving said plunger to expel a dose and for moving said shield portion to its locked out extended position, whereby, on completion of an injection operation, said disposable syringe assembly may be removed from said autoinjector in a shielded condition for subsequent disposal.

Thus on completion of injection the syringe is shielded to allow safe disposal, and the number of components thrown away is low, thereby reducing environmental impact. The safety shield arrangement may also be used to shield a syringe that is used manually.

Thus, in another aspect there is provided a safety shield arrangement for use with a syringe having a syringe barrel, a needle at the forward end of the barrel and a plunger, said arrangement comprising:

a syringe housing for being coupled to said syringe barrel in use and restrained against longitudinal movement with respect thereto, a shield portion mounted for a generally telescopic movement relative to said syringe housing between a retracted position and an extended shielding position in which in use it shields said syringe needle, and a lock out arrangement effective as said shield moves towards its extended position to prevent retraction therefrom.

Preferably said syringe housing has engagement means resiliently to retain the syringe therein, such as for example surfaces providing a snap-fit for ease of assembly.

The lock out arrangement may comprise a resiliently deformable latch on one of said syringe housing and said shield portion, with the latch being snap-engageable with a latch surface on the other of said syringe housing and said shield portion. The extent of forward extension movement of said shield relative to said syringe housing may be limited by cooperating stop surfaces. A latch may be provided for releasably retaining the shield portion in a retracted position prior to forward extension thereof.

Where an autoinjector is used with a syringe with a safety shield which is subsequently disposed of, such that the needle shield is not a permanent component of the autoinjector, the sequencing of operation of the autoinjector is an important aspect.

Thus in yet another aspect there is provided an autoinjector adapted to receive in use a removable syringe assembly, including a syringe having a barrel, a needle at the forward end of the barrel and a plunger for expelling a dose through said needle, and a shield for being moved forwardly to shield the needle after injection, said device comprising:

a housing, a drive mechanism including a drive member releasable for forward movement in use to drive said syringe plunger forwardly, a syringe carriage for imparting forward movement of the syringe barrel relative to said housing, a shield carriage for imparting forward movement of the shield relative to said syringe carriage, and a control element associated with said drive member arranged to prevent forward movement of said shield carriage until after release of said drive member.

The autoinjector preferably includes a syringe carriage bias means urging the syringe carriage forward relative to the housing, with there also being shield carriage bias means for urging said shield carriage forwardly relative to said syringe carriage. In this way the movement of the syringe and shield during the injection stages is assisted by the respective biases. Advantageously, said control element cooperates with said drive member and at least one of said syringe carriage and said shield carriage when the drive member is in a primed position to retain both the syringe carriage and the shield carriage in retracted positions but when released allows movement of both relative to the drive member and to each other, such that each is independently movable.

Whilst the invention has been described above, it extends to any inventive combination of the features set out above, or in the following description or claims.

BRIEF DESCRIPTION OF THE DRAWINGS

The invention may be performed in various ways, and an embodiment thereof will now be described by way of example only, reference being made to the accompanying drawings in which:

FIGS. 4(a), (b) and (c) are detailed views on the end of the syringe housing with the housing alone, with the housing, syringe and shield and on the shield alone;

FIGS. 5(a) and (b) are detailed views showing the latching arrangement for releasably latching the shield in a retained position on the syringe housing;

FIGS. 6(a) and (b) are views on the underside of the syringe housing and the shield respectively showing the lock out features;

FIGS. 7(a) and (b) are detailed sectional views showing the shield releasably latched in its retracted position and locked out in its extended position respectively;

FIGS. 13(a) and (b) show the syringe carriage and shield driver in the loaded position, when viewed from above and below respectively;

FIGS. 14(a) and (b) are views on the syringe carrier and shield driver when in the fired position taken from above and below respectively;

FIGS. 15(a) and (b) are detailed views of the shield carriage and its engagement with the shield respectively;

FIGS. 16(a) and (b) are perspective side and rear views of the components that apply drive to the syringe plunger, the syringe barrel and the shield taken from one side and below respectively in the loaded position;

FIGS. 17(a) and (b) are views similar to FIGS. 16(a) and (b) but showing the components in the fired position;

FIGS. 18(a), (b) and (c) are detailed views on the trigger assembly of the autoinjector, and FIGS. 19 (a) to (f) are views showing the cycle of operation of the autoinjector of FIGS. 9 to 18.

DETAILED DESCRIPTION OF THE INVENTION

Referring initially to FIGS. 1 to 7, a safety syringe shield arrangement will firstly be described. This arrangement is designed to be fitted in the autoinjector that is later described with reference to FIGS. 8 to 19 but it also may be used to provide shielding for manual use syringes.

Figures 1, 2:
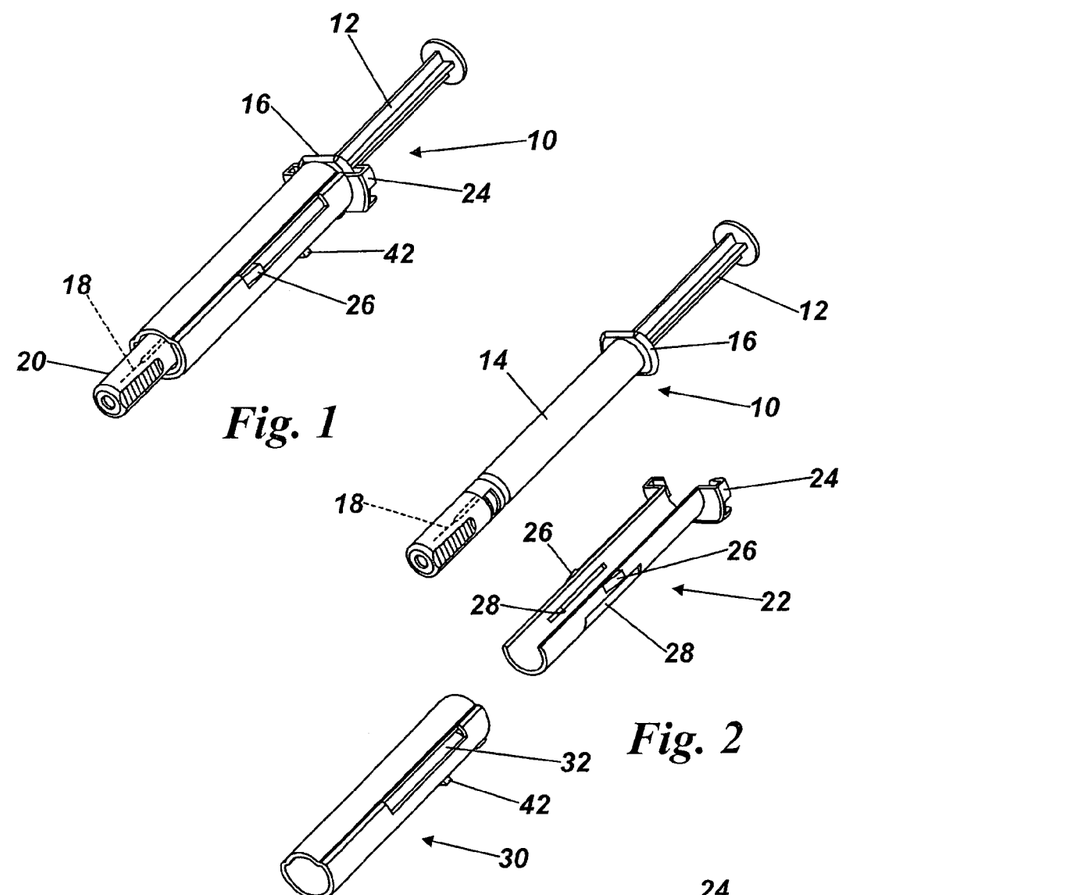
FIG. 1 is a general perspective view of a syringe fitted with a safety shield in accordance with this invention, for use in an autoinjector or manually.
FIG. 2 is an exploded view of the arrangement of FIG. 1.
Figure 3:
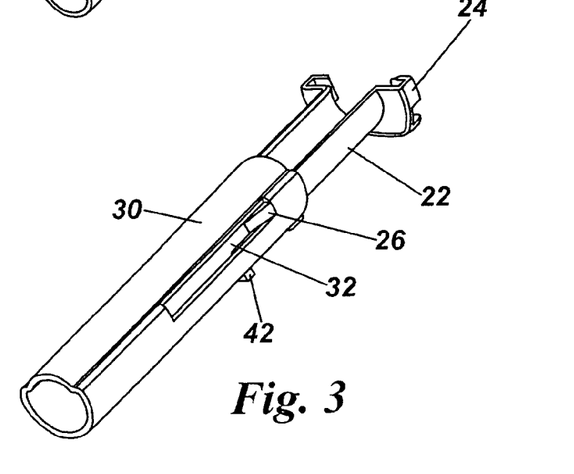
FIG. 3 is a view similar to FIG. 1 but with the syringe removed and the shield fully extended.
Figure 4:
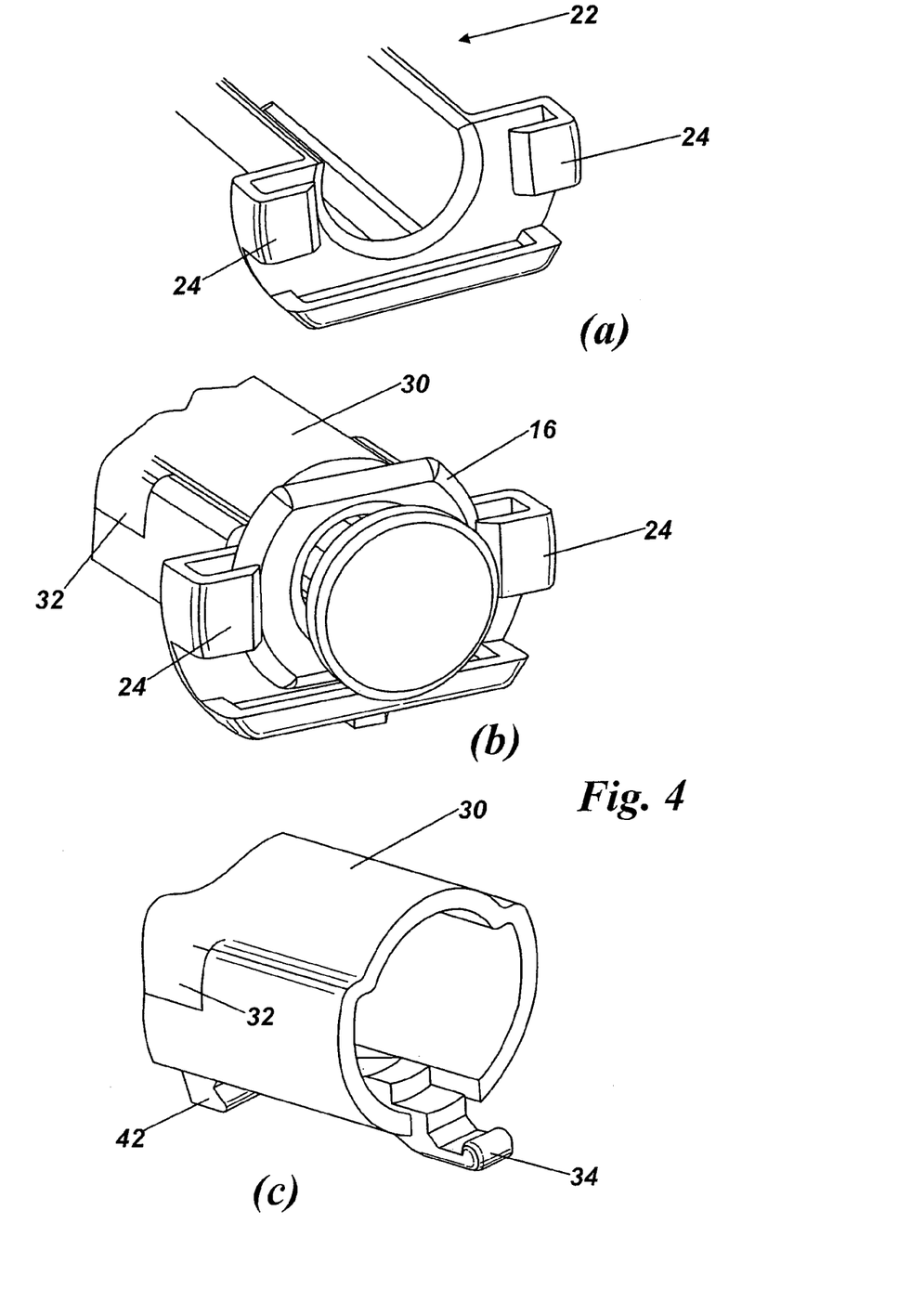
Figure 5:
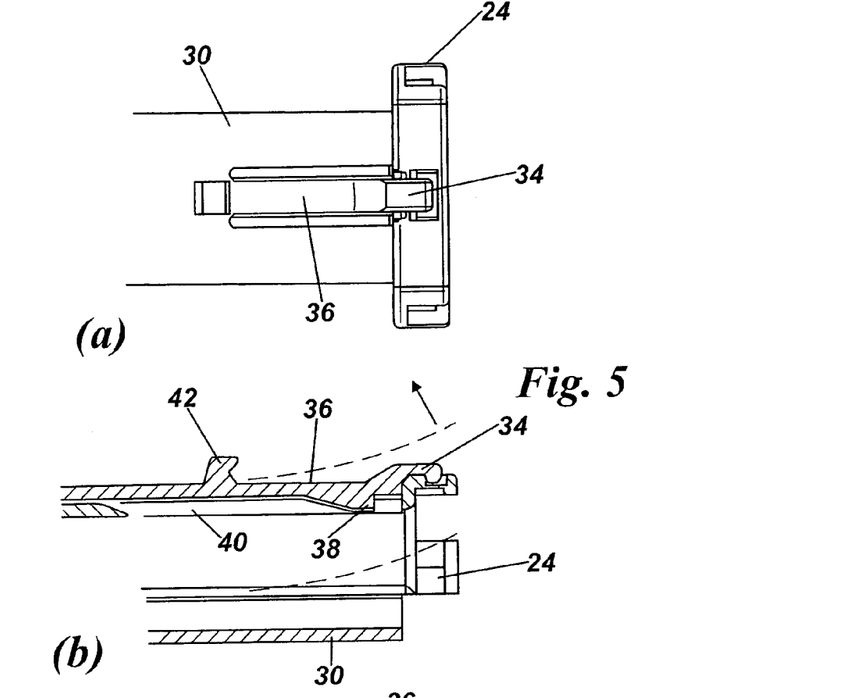

In FIG. 1, there is shown a syringe 10 having a plunger 12, a barrel 14 (see FIG. 2) with an outturned flange 16 with the syringe needle being covered prior to injection by a cap 18. The syringe is fitted inside a shroud assembly comprising a syringe carrier 22 of open trough form having a fitting 24 at its rear end for engaging the flange 16 of the syringe barrel and having outwardly directed barbs 26 connected on thin flexible strips defined by slits 28 in the carrier. The shield 30 has a lower cylindrical portion of diameter to fit telescopically over the carrier 22 and an upper cylindrical portion of slightly lesser diameter designed telescopically to slide over the barrel of the syringe 14. The shield has two slots 32 which, when the syringe carrier 22 is slid inside the shield 30 cooperate with the barbs 26 to limit extension movement of the shield 30. The slits 28 on the syringe carrier allow the barbs 26 to deflect inwardly to allow assembly but, once the syringe 10 is inserted inward deflection of the barbs is prevented by the syringe barrel 14.

FIGS. 4(a), (b) and (c) are detailed views on the end showing how the flange of the syringe can be snapped into engagement with the fitting 24. Also visible in FIG. 4(c) is a retention latch 34 which lightly clips the shield 30 in a retracted position relative to the syringe carrier 22. This can be seen in more detail in FIGS. 5 and 6. It will be seen that the retention latch 34 is at the end of a flexible finger 36 which allows the latch to disengage when sufficient pull is applied to the shield 30. The retention latch engages in a recess 36 forming part of the end fitting of the syringe carrier 22.

Figure 6:
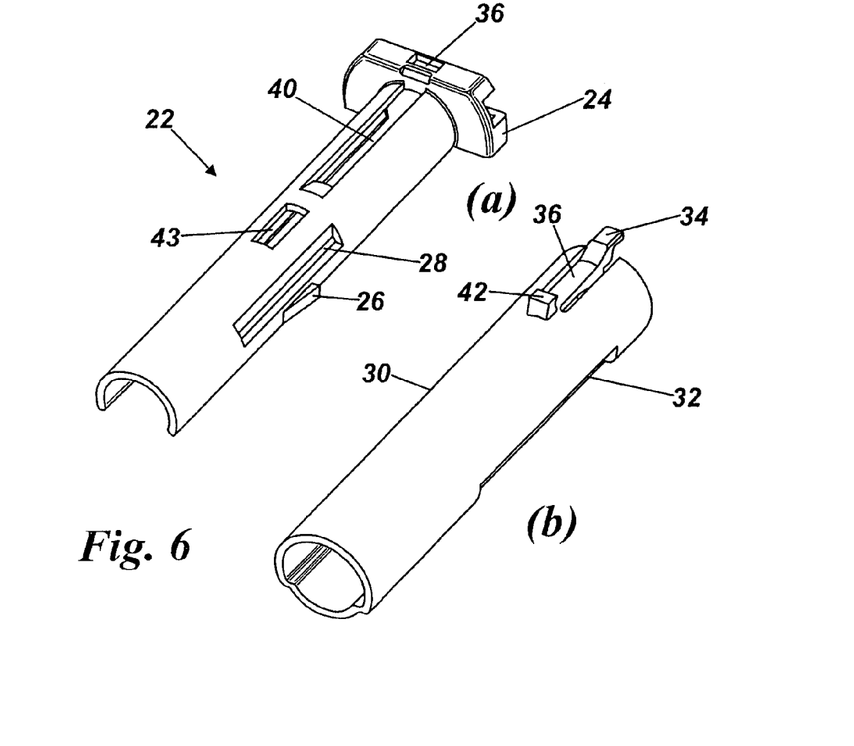
Figure 7:
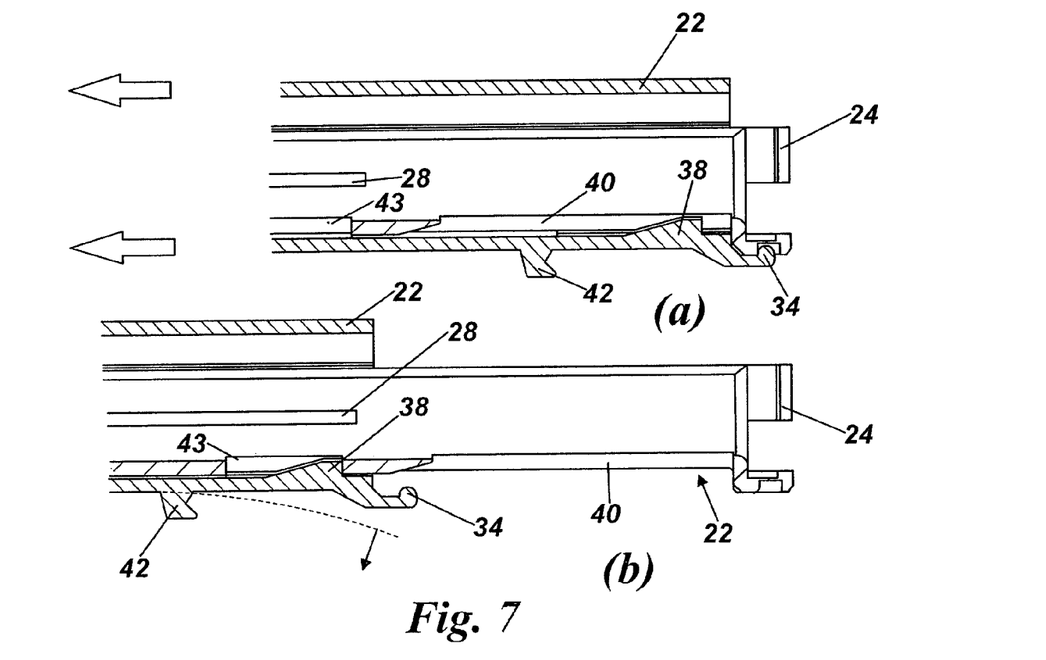

Referring now in more detail to FIGS. 6 and 7, the radially inner surface of the finger 36 is provided with a lock out latch 38 that runs in a slot 40 on the syringe carrier. At its forward end, the slot 40 terminates in a ramp surface, forwardly of which is a lock out recess 43. Forward of the flexible finger 36, and on a relatively inflexible portion of the shield 30, is a drive lug 42 for use in the autoinjector to drive the shield forward on completion of an injection.

The above syringe safety shield arrangement therefore allows the syringe to be snap-fitted into the syringe carrier 22 and, after injection, the shield 30 to be pulled forwardly until locked out by engagement of the lock out latch 38 in the lock out recess 43.

Referring now to the autoinjector 50 illustrated in FIGS. 8-17, this includes an outer casing 52 closed at the rear end but providing an open access forward end into which a module comprising a syringe fitted into the safety shield described above can be fitted for injection. The autoinjector is primed by sliding a cover portion 54 rearwardly to cock a plunger 56, the arrangement is then fired by pushing a button 58 on the rear end of the device sub-flush.

Figure 8:
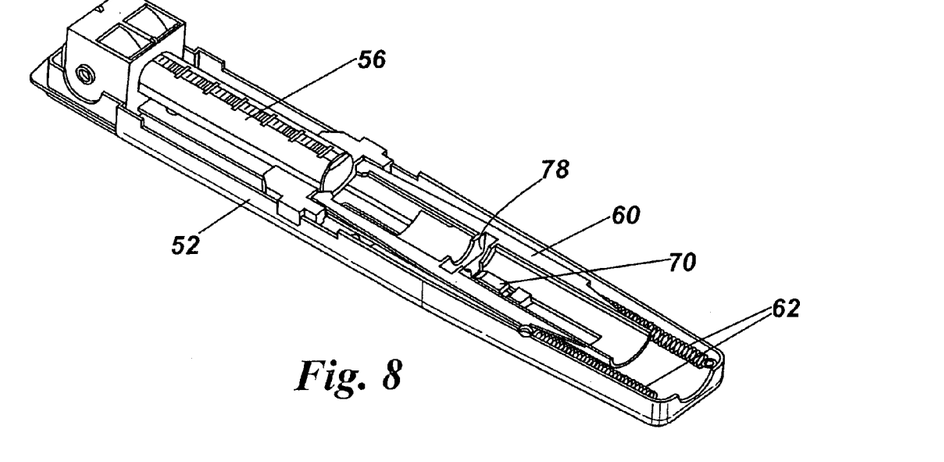
FIG. 8 is a top perspective view of an autoinjector for receiving the syringe safety shield arrangement of FIG. 1, but with the upper housing of the autoinjector removed.
Figure 9:
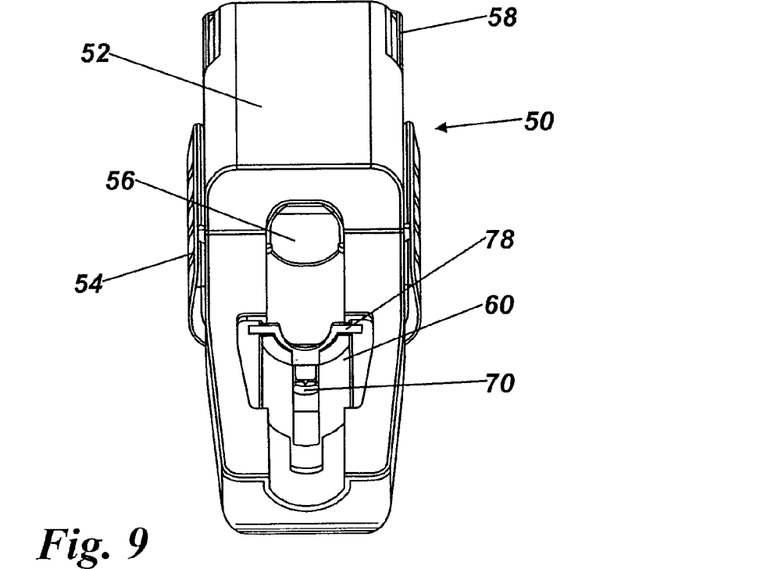
FIG. 9 is a perspective view from the front and above of the autoinjector of FIG. 8, but with the upper housing in place.
Figure 10:
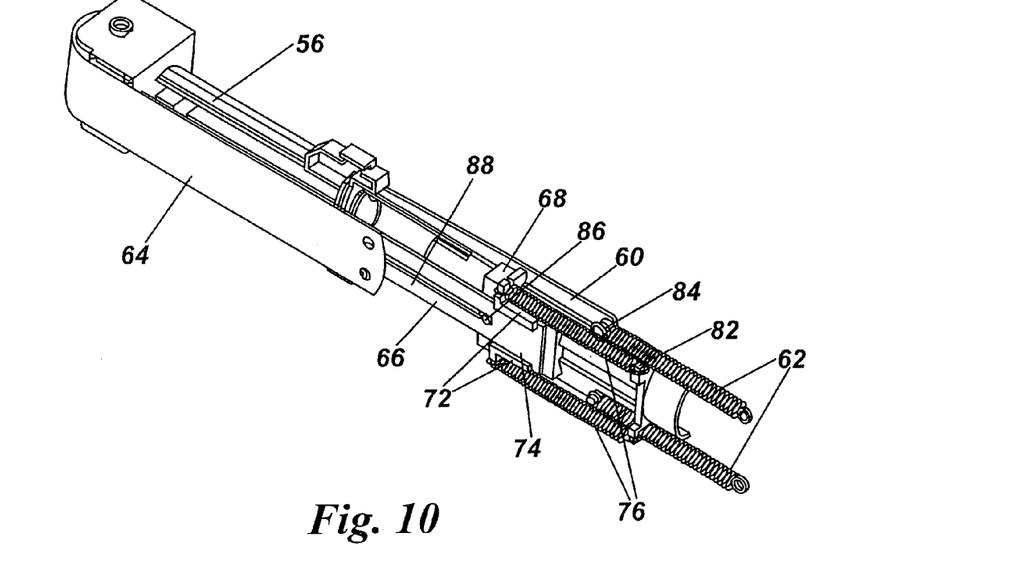
FIG. 10 is a view on the main drive components of the autoinjector of FIGS. 8 and 9 removed from the autoinjector housing and rotated through 90°.
Figure 11:
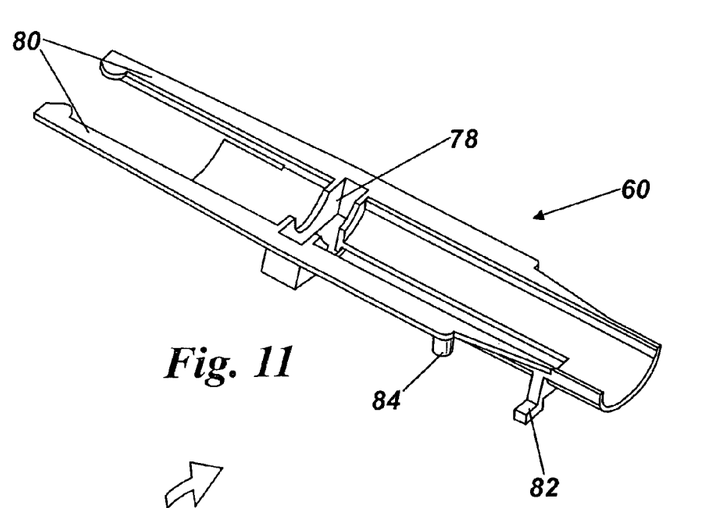
FIG. 11 is a perspective view from above of the syringe carriage.
Figure 12:
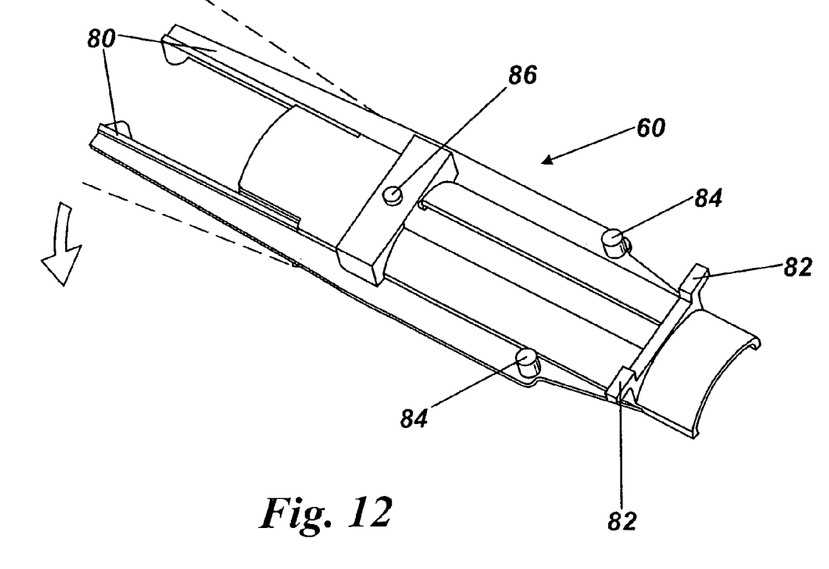
FIG. 12 is a perspective view from below of the syringe carriage.
Figures 13, 14:
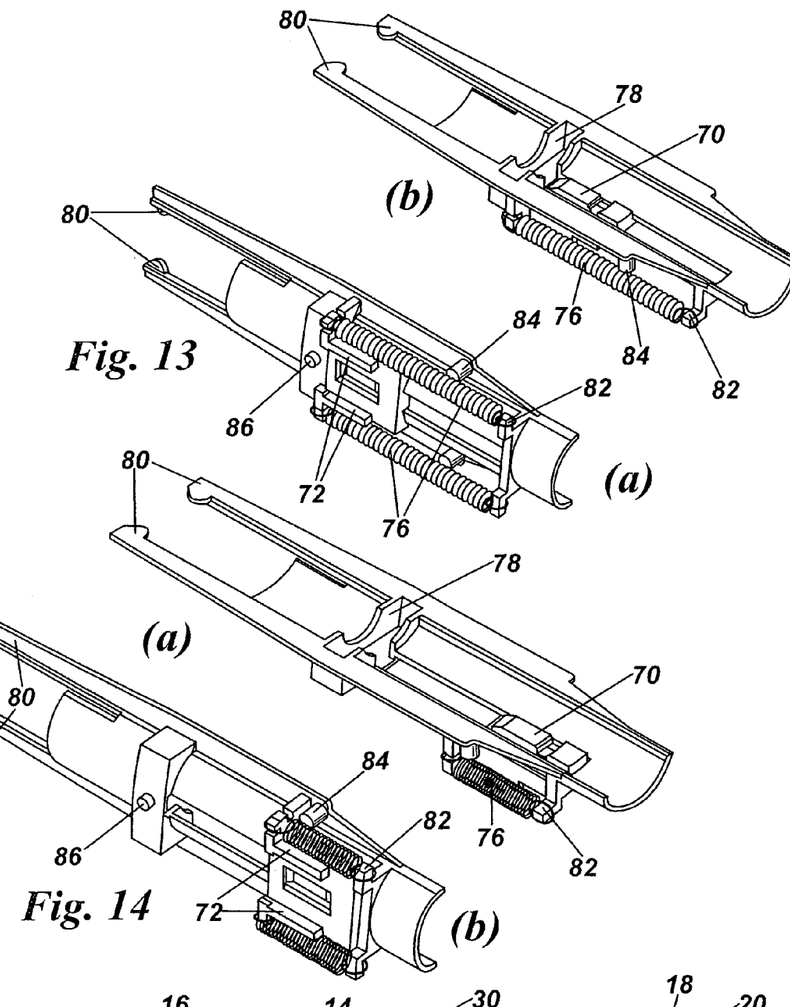
Figure 15:
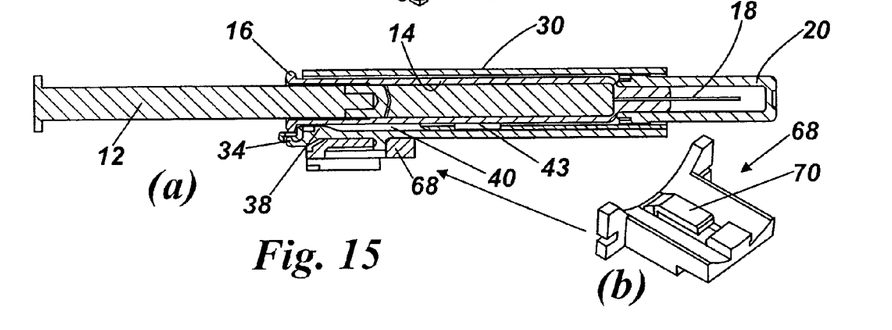
Figure 16:
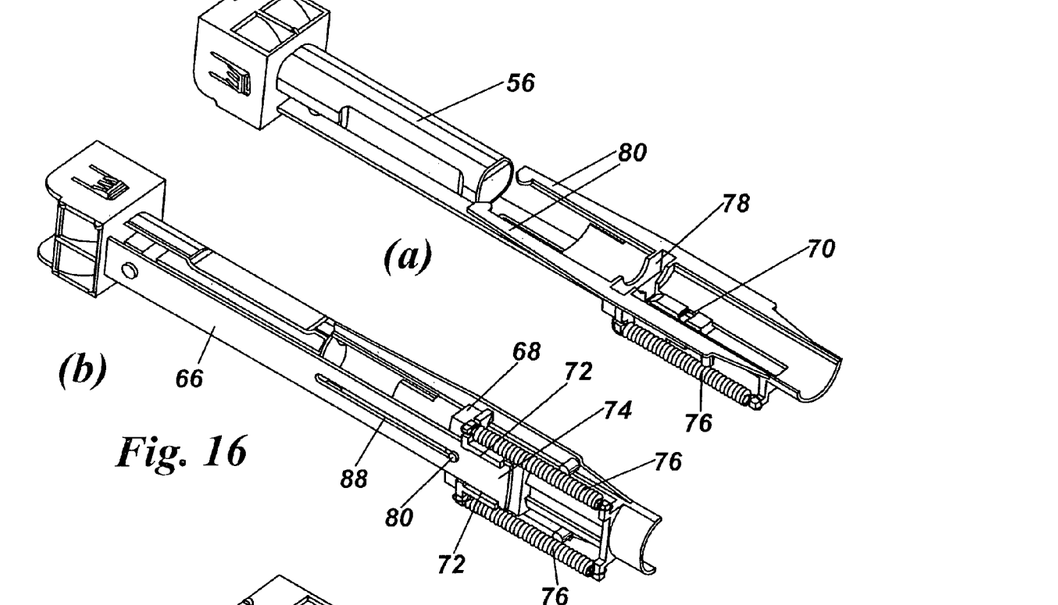
Figure 17:
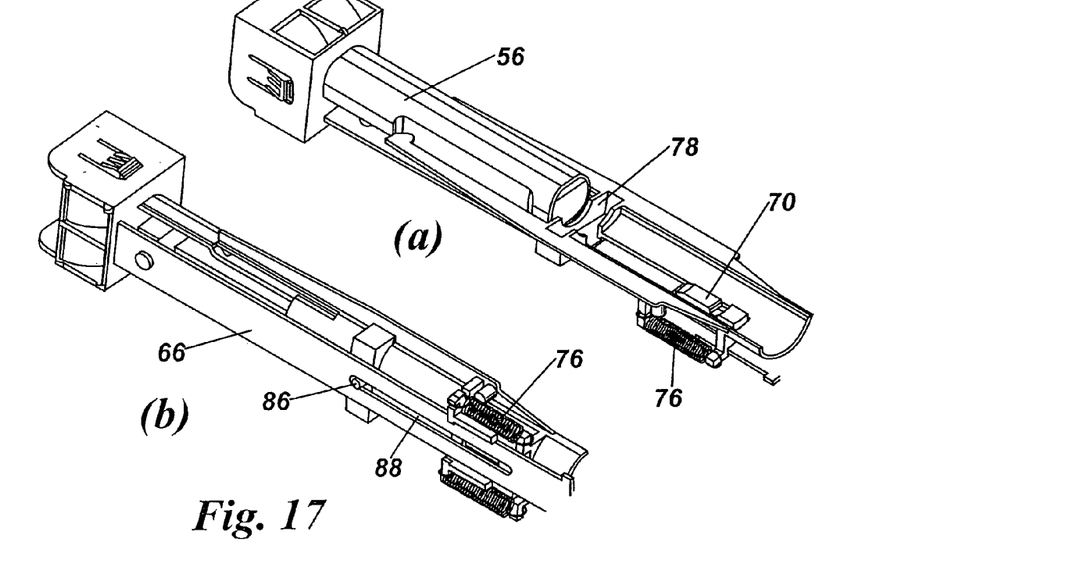

Referring to FIGS. 8 and 10, inside the casing is mounted a syringe carriage 60 which is biased forwardly by twin syringe carriage springs 62. The plunger 56 is urged forward by a constant force spring 64, the front end of which is anchored on the inside of the housing 52. A slotted reset arm 66 is secured to the plunger and moves longitudinally with it, to control movement of the syringe and various components to be described below. A shield carriage 68 is slideably disposed on the underside of the syringe carriage and has a drive interface 70 designed to receive in use the drive lug 42 of the shield 30 in a releasable snap-fit. The shield carriage has twin side ribs 72 which cooperate with a T-shaped formation 74 on the forward end of the reset arm 66. The shield carriage 68 is biased forwardly by twin shield carriage springs 76. The inner surface of the syringe carriage 60 has an arcuate recess 78 designed to receive the end fitting 24 on the syringe carrier 22. Extending rearwardly from the arcuate recess 78 are twin flexible arms 80 which engage within the housing. On the underside of the syringe carriage are provided laterally extending anchorage lugs 82 on which the forward ends of the shield carriage springs 76 are anchored. To the rear of the lateral anchorage lugs 82 are two downwardly extending anchorage lugs 84 on which the rear ends of the syringe carriage springs are anchored. On the underside of the formation defining the annular recess 78 is a peg 86 which slides in a slot 88 in the slotted reset arm 66.

The reset arm 66 provides a sequencing function, restraining the syringe carriage 60 and the shield carriage 68 against forward movement until the plunger 56 has been released to move forwardly under the influence of the constant force spring 64. Thus, in the primed state shown in FIG. 10, the plunger is in its rearward position and engagement of the peg 86 on the syringe carriage in the forward end of the slot 62 restrains movement of the syringe carriage under the influence of the carriage springs 62. In addition, engagement of the T-formation 74 with the rib 72 on the shield carriage means that the shield carriage is prevented from forward movement with respect to the syringe carriage. The reset arm in this position therefore retains both the syringe carriage and the shield carriage in fully retracted positions. However, once the plunger is released and driven forwardly by the constant force spring 64, the reset arm 66 moves forward thus allowing the syringe carriage and the shield carriage to move forwardly under the influence of their respective carriage springs. When freed the syringe carriage and the shield carriage are free to move forwardly relative to the housing and to move relatively to each other. Once the syringe carriage reaches its forwardmost position it stops and the plunger 56 then engages the syringe plunger to expel a dose. Upon removing the autoinjector from the injection site, the residual bias in the shield carriage springs 76, pulls the shield forwardly to shield the needle, and to lock out. FIGS. 17(a) and (b) show the components in this condition, with the syringe removed. It will be seen here that the plunger 56 is extended, and the drive interface 70 is at the forward end limit of its travel.

Figure 18:
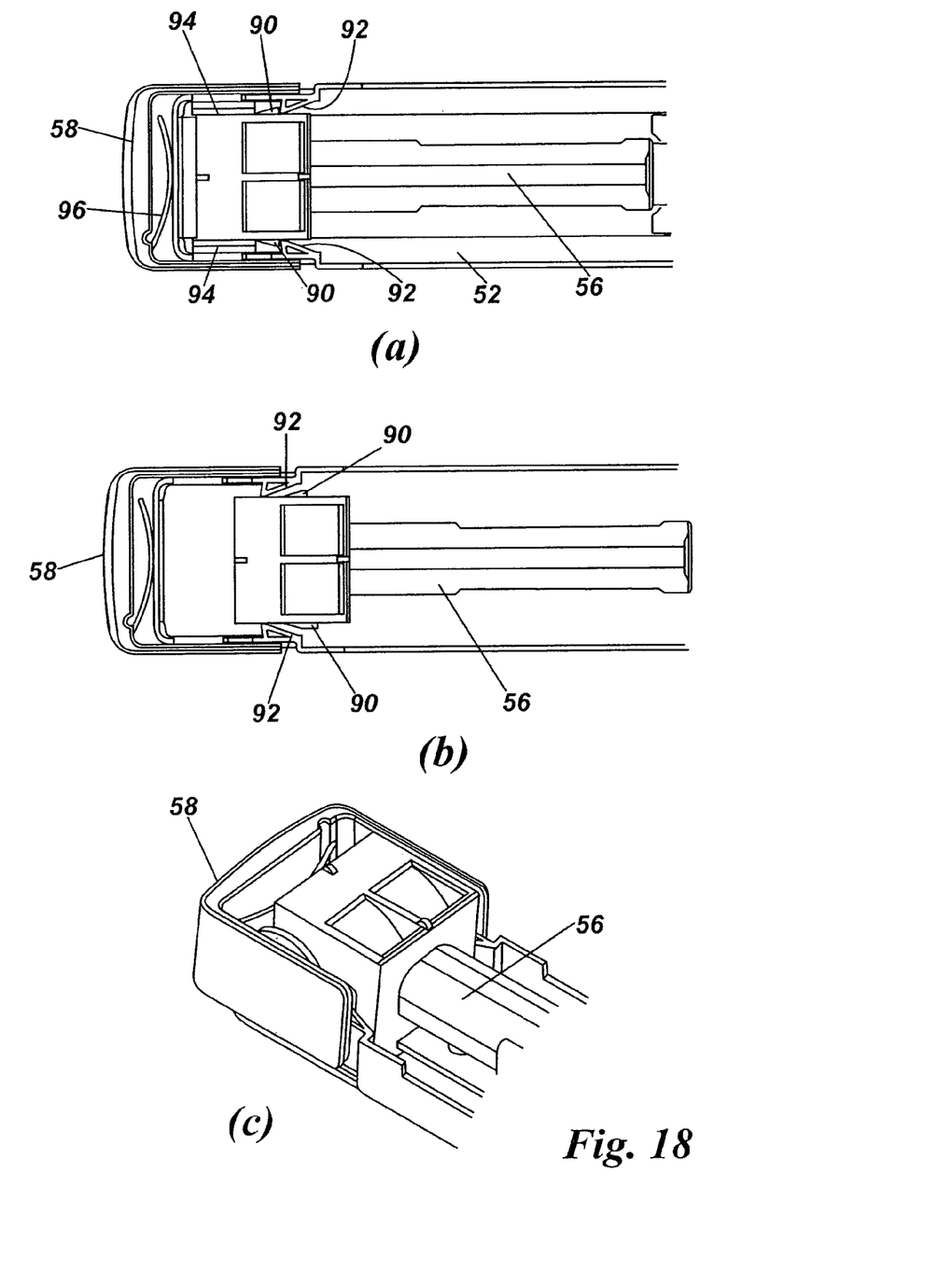
Figure 19:
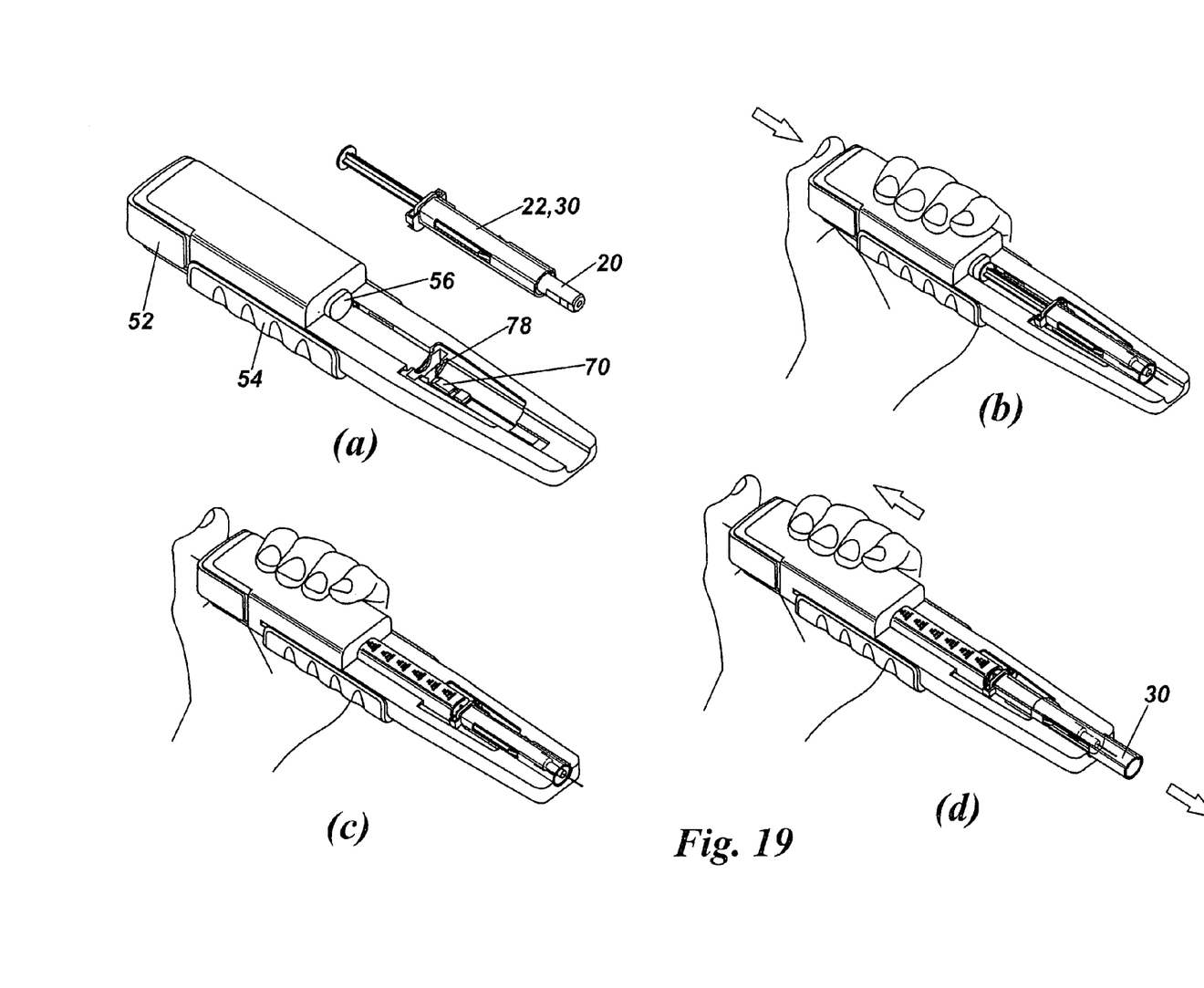

FIGS. 18 (a) to (c) show the trigger arrangement in this embodiment. The drive plunger 56 has two flexible barbs 90 that can slide past and be captured by complementary barbs 92 on the inner wall of the housing, to retain the plunger in an energised position when pulled back against the spring bias of the constant force spring 64. The firing button 58 is connected to an inner sleeve 94 which, when the firing button 58 is pressed against the bias of a leaf spring 96 squeezes the barbs 90 inwardly so they disengage from the barbs 92 on the housing, thus allowing the plunger to move forward under the influence of the constant force spring 64.

Referring now to FIGS. 19(a) to (f) the operation of the autoinjector will now be described. In FIG. 19(a) a syringe with a safety shield arrangement as described above is fitted into an autoinjector which has been previously primed by sliding back the cover 54. The syringe is located by inserting it into the syringe carriage with the fitting 24 being received in the recess 78 and the drive lug 42 on the shield being received in the drive interface 70. The device is offered up to the injection site (FIG. 19(b)) and the trigger depressed. The plunger 56 shoots forward allowing the syringe carriage and the shield carriage to move the syringe and shield assembly forward. On reaching its forwardmost position, the syringe carriage is arrested and the plunger 56 then expels a dose from the syringe (FIG. 19(c)). Upon then removing the autoinjection from the injection site, the needle shield is moved forwardly by the shield carriage moving forwardly relative to the syringe carriage (FIG. 19(d)) until the needle shield is fully extended and locked out by the lock out latch 38 latching into the lock out recess 43. The syringe with the safety shield extended and locked out may then be removed (FIG. 19(d)) and disposed of safely. The autoinjector may then be re-primed by sliding the cover 54 rearwardly (FIG. 19(e)).

The invention claimed is:

1. An autoinjector system comprising an autoinjector device having a housing comprising an interface configured for detachably receiving a disposable syringe assembly, the disposable syringe assembly comprising a syringe having a syringe barrel, a needle at the forward end, and a plunger, the syringe assembly further including a safety shield arrangement, comprising:
   a syringe housing receiving said syringe barrel and restrained against longitudinal movement with respect thereto,
   a shield portion mounted for generally telescopic movement relative to said syringe housing between a retracted position and an extended position in which in use it shields said syringe needle, and
   a lock out arrangement effective as said shield moves towards said extended position to prevent retraction therefrom,
   the autoinjector including a drive mechanism for advancing said syringe to an injection position, for driving said plunger to expel a dose and for moving said shield portion to said locked out extended position,
   whereby, on completion of an injection operation, said disposable syringe assembly may be detached from said autoinjector housing interface in a shielded condition for subsequent disposal.

2. A safety shield arrangement for use with a syringe having a syringe barrel, a needle at the forward end of the barrel and a plunger, said arrangement comprising:
   a syringe housing for being coupled to said syringe barrel in use and restrained against longitudinal movement with respect thereto,
   a shield portion mounted for a generally telescopic movement relative to said syringe housing between a retracted position and an extended shielding position in which in use it shields said syringe needle, and
   a lock out arrangement provided between said syringe housing and said shield portion and effective as said shield portion moves towards said extended position to prevent retraction therefrom.

3. A safety shield according to claim 2, wherein said syringe housing has engagement means resiliently to retain the syringe therein.

4. A safety shield arrangement according to claim 3, wherein said lock out arrangement comprises a resiliently deformable latch on one of said syringe housing and said shield portion, said latch being snap-engageable with a latch surface on the other of said syringe housing and said shield portion.

5. A safety shield arrangement according to claim 3, wherein cooperating stop surfaces are provided to limit the extent of forward extension movement of said shield relative to said syringe housing.

6. A safety shield arrangement according to claim 3, including a latch for releasably retaining the shield portion in a retracted position prior to forward extension thereof.

7. A safety shield arrangement according to claim 2, wherein said lock out arrangement comprises a resiliently deformable latch on one of said syringe housing and said shield portion, said latch being snap-engageable with a latch surface on the other of said syringe housing and said shield portion.

8. A safety shield arrangement according to claim 7, wherein cooperating stop surfaces are provided to limit the extent of forward extension movement of said shield relative to said syringe housing.

9. A safety shield arrangement according to claim 7, including a latch for releasably retaining the shield portion in a retracted position prior to forward extension thereof.

10. A safety shield arrangement according to claim 2, wherein cooperating stop surfaces are provided to limit the extent of forward extension movement of said shield relative to said syringe housing.

11. A safety shield arrangement according to claim 2, including a latch for releasably retaining the shield portion in a retracted position prior to forward extension thereof.

12. An autoinjector adapted to receive in use a removable syringe assembly including a syringe having a syringe barrel, a needle at the forward end of the barrel and a plunger for expelling a dose through said needle, the assembly further including a shield for being moved forwardly to shield the needle after injection, said device comprising:
   a housing comprising an interface configured for detachably receiving in use said removable syringe assembly,
   a drive mechanism including a drive member releasable for forward movement in use to drive said syringe plunger forwardly,
   a syringe carriage for imparting forward movement of the syringe relative to said housing,
   a shield carriage for imparting forward movement of the shield relative to said syringe carriage, and
   a control element associated with said drive member arranged to restrain forward movement of said shield carriage relative to said syringe carriage until after release of said drive member.

13. An autoinjector according to claim 12, including a syringe carriage bias means urging the syringe carriage forward relative to the housing.

14. An autoinjector according to claim 13, including shield carriage bias means for urging said shield carriage forwardly relative to said syringe carriage.

15. An autoinjector according to claim 13, wherein said control element cooperates with said drive member and at least one of said syringe carriage and said shield carriage, when the drive member is in a primed position to retain both the syringe carriage in respective retracted positions, but when released allows movement of both relative to the housing and to each other.

16. An autoinjector according to claim 12, including shield carriage bias means for urging said shield carriage forwardly relative to said syringe carriage.

17. An autoinjector according to claim 16, wherein said control element cooperates with said drive member and at least one of said syringe carriage and said shield carriage, when the drive member is in a primed position to retain both the syringe carriage in respective retracted positions, but when released allows movement of both relative to the housing and to each other.

18. An autoinjector according to claim 12, wherein said control element cooperates with said drive member and at least one of said syringe carriage and said shield carriage, when the drive member is in a primed position to retain both the syringe carriage in respective retracted positions, but when released allows movement of both relative to the housing and to each other.

19. An autoinjector adapted to receive in use a removable syringe assembly including a syringe barrel having a syringe, a needle at the forward end of the barrel and a plunger for expelling a dose through said needle, the assembly further including a shield for being moved forwardly to shield the needle after injection, said device comprising:
   a housing comprising an interface configured for detachably receiving in use said syringe assembly,
   a drive mechanism including a drive member releasable for forward movement in use to drive said syringe plunger forwardly,
   a syringe carriage for imparting forward movement of the syringe relative to said housing,
   a shield carriage for imparting forward movement of the shield relative to said syringe carriage.

\* \* \* \* \*